United States Patent
Troyer et al.

(10) Patent No.: US 10,123,517 B2
(45) Date of Patent: Nov. 13, 2018

(54) IMMUNE COMPETENT MODELS OF HUMAN DISEASE

(71) Applicant: Kansas State University Research Foundation, Manhattan, KS (US)

(72) Inventors: Deryl Troyer, Manhattan, KS (US); Duane Davis, Westmoreland, KS (US); Stefan Bossmann, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 54 days.

(21) Appl. No.: 15/135,244

(22) Filed: Apr. 21, 2016

(65) Prior Publication Data

US 2016/0235044 A1 Aug. 18, 2016

Related U.S. Application Data

(63) Continuation-in-part of application No. PCT/US2014/061937, filed on Oct. 23, 2014.

(60) Provisional application No. 61/895,018, filed on Oct. 24, 2013.

(51) Int. Cl.
| | |
|---|---|
| *A01K 67/00* | (2006.01) |
| *C12N 5/02* | (2006.01) |
| *C12N 15/00* | (2006.01) |
| *A01K 67/027* | (2006.01) |
| *A61K 49/00* | (2006.01) |
| *A61K 35/12* | (2015.01) |

(52) U.S. Cl.
CPC ...... *A01K 67/0271* (2013.01); *A61K 49/0008* (2013.01); *A01K 2207/12* (2013.01); *A01K 2207/15* (2013.01); *A01K 2227/105* (2013.01); *A01K 2227/108* (2013.01); *A01K 2267/0331* (2013.01); *A61K 35/12* (2013.01); *A61K 2035/122* (2013.01)

(58) Field of Classification Search
CPC .. A01K 7/0271; A01K 2207/12; A61K 35/12; A61K 2035/122; A61K 49/0008
USPC ........................................ 800/8, 21; 435/325
See application file for complete search history.

(56) References Cited

U.S. PATENT DOCUMENTS

| | | | | |
|---|---|---|---|---|
| 5,723,718 | A * | 3/1998 | Berens ............... | A01K 67/0271 424/93.1 |
| 6,060,049 | A * | 5/2000 | Beschorner ........ | A01K 67/0271 424/577 |
| 2005/0005312 | A1* | 1/2005 | Wu et al. | |
| 2010/0099638 | A1 | 4/2010 | Fu | |

OTHER PUBLICATIONS

Turrini et al., 2005, Biochemical and Biophysical Research Communication, vol. 326, p. 66-73.*
The International Search Report and Written Opinion dated Jan. 21, 2015, in PCT/US2014/061937 filed Oct. 23, 2014.
Turrini, Pailo "Human Hepatocytes in Mice Receiving Pre-immune injection with human cord blood cells" Biochemical and Biophysical Research Communications 326 (2005) 66-73.

* cited by examiner

*Primary Examiner* — Shin Lin Chen
(74) *Attorney, Agent, or Firm* — Hovey Williams LLP

(57) ABSTRACT

Immunocompetent animal models having immunological tolerance to a xenograft and methods of producing the same. The animal models are tolerized to the xenograft in the pre-immune, fetal or embryonic stage, followed by transplanting the xenograft into the animal in the post-natal stage, such that the post-natal animal is immunologically tolerant to the xenograft, while remaining immunocompetent.

13 Claims, 9 Drawing Sheets
(9 of 9 Drawing Sheet(s) Filed in Color)

IMMUNE COMPETENT MODELS OF HUMAN DISEASE

CROSS-REFERENCE TO RELATED APPLICATIONS

The present application is a continuation-in-part of International Application Serial No. PCT/US2014/061937, filed Oct. 23, 2014, which claims the priority benefit of U.S. Provisional Patent Application Ser. No. 61/895,018, filed Oct. 24, 2013, entitled LARGE ANIMAL MODELS OF HUMAN CANCERS, each incorporated by reference in its entirety herein.

BACKGROUND OF THE INVENTION

Field of the Invention

The present invention relates to immunocompetent animal models that are immunologically tolerant to xenogenic tissue, and methods of making and using the same.

Description of Related Art

There is a tremendous demand for more sophisticated animal models for preclinical testing that more closely reflect the human body. Many preclinical therapies that are tested in rodents fail miserably when they get to human trials. Thus, having convincing data in an "intermediate" species would be of tremendous value in the decision tree for taking a product or idea forward. These studies would also significantly enhance the prospects for INDs and clinical trials. No such models exist in the pig or other large animals as tumors are almost impossible to initiate in the fetal animal. Transgenic animals are difficult to produce since efficient embryonic stem cells or homologous recombination methods are not available. Severe combined immune-deficient (SCID) animals are difficult and expensive to raise and have issues when used as disease models. It would be greatly advantageous to have access to "tolerogenic," or immunologically tolerant, animals for human cellular transplants of cancer cells or other cells for disease modeling.

SUMMARY OF THE INVENTION

The present invention is broadly concerned with methods of producing an immunocompetent animal model having immunological tolerance to a xenograft. The method comprises transplanting a first xenogenic tissue into a pre-natal recipient animal. The pre-natal recipient animal is a pre-immune, fetal or embryonic non-human animal. The pre-natal recipient animal is then allowed to develop into a post-natal recipient animal. The method further comprises transplanting a second xenogenic tissue into the post-natal recipient animal. The second xenogenic tissue is from the same source as the first xenogenic tissue. Advantageously the post-natal recipient animal is immunocompetent and immunologically tolerant to the transplanted xenogenic tissue.

Immunocompetent animal models produced according to methods of the invention are also described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
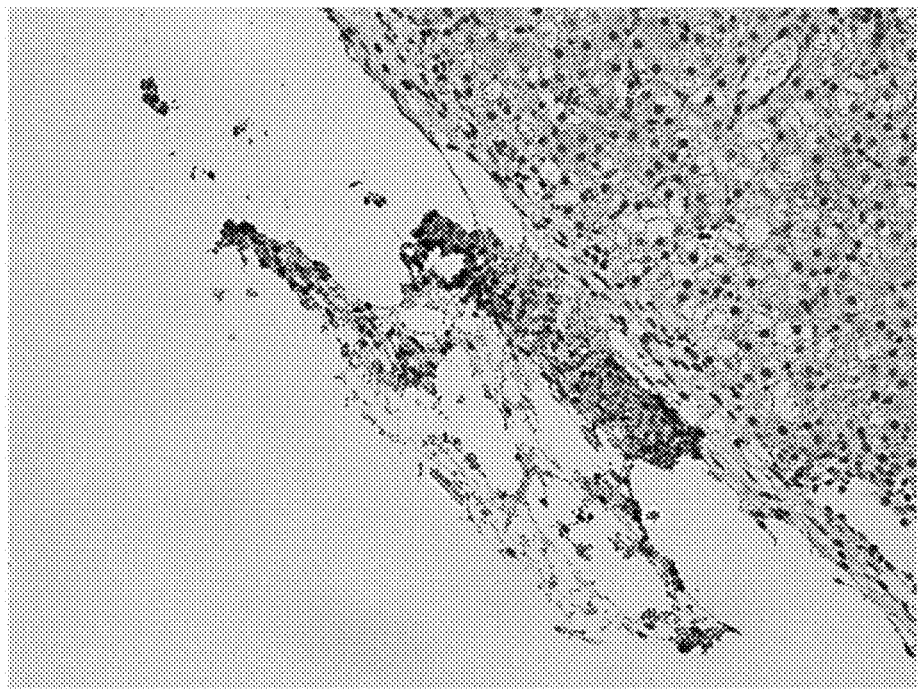
FIG. 1 is an image of a newborn piglet liver sectioned and fixed in paraformaldehyde and analyzed using immunohistochemistry (IHC) with an antibody specific for human nuclei (brown)

The present invention is concerned with non-human animal models rendered immunologically tolerant to a xenograft, while maintaining a competent immune system. The animal models are "tolerogenic" to the xenograft, which means they are immunologically tolerant such that they maintain a state of tolerance to the xenogenic tissue, instead of mounting an immune response to, or rejection of, the foreign tissue. The term "tolerogenic," in the context of the present application, further means that the animals tolerate the xenograft, without being immunocompromised or immunodeficient, either through the use of genetic modifications or immunosuppressive agents. Thus, an immunodeficient or immunocompromised animal is one where the natural or native immune response is attenuated, weakened, or decreased, such that the animal has an altered immunocompetence to fight a foreign antigen. Such animals usually lack or have atypical T, B, and/or NK cells. In contrast, an "immunocompetent" animal, as used herein, is one in which the native or natural innate and adaptive immune system has been retained (i.e., not artificially altered), such that the animal retains its normal capacity to develop an immune response against a foreign antigen—the advantage being that the inventive animal models have been tolerized specifically to certain xenogenic tissue, such that they do not recognize such xenograft as a foreign tissue. Therefore, xenotransplantation and engraftment can be achieved without the need to resort to genetic modification of the recipient animal's native immune system or the use of immunosuppressive agents to prevent the animal from rejecting the xenograft. A further advantage is that the animal remains capable of mounting a normal immune response against pathogens and infection. Thus, such immunocompetent animals would usually have T, B, and/or NK cells that are normal and/or unaltered (insofar as being not artificially altered or engineered, it being appreciated that a natural mutation may arise, which otherwise does not significantly impair the animal's normal immune response).

The term "xenograft" is used interchangeably herein with "xenogenic tissue," and refers to cells or tissues originating from a different species than the recipient animal. In the inventive method, the xenogenic tissue is first transplanted into a pre-natal recipient animal. The term "pre-natal" as used herein refers to the animal in the fetal stage of development (or embryonic stage, depending on the species), which for the majority of animals, is before birth or hatching. Exceptions include certain fish that hatch as embryos. More particularly, the xenogenic tissue is transplanted into the pre-natal recipient animal during gestation (or incubation). The first xenogenic tissue will typically be transplanted via injection (for example, into the peritoneal cavity or amniotic sac/amnion/amniotic fluid/cavity of the pre-natal recipient animal). That is, the first xenogenic tissue is preferably not transplanted/injected directed into the pre-natal recipient animal. Depending on the species, access to the pre-natal animal in the womb of the maternal animal can be achieved using minimally invasive techniques, such as by ultrasound-guided transcutaneous injection, endoscopy, and/or laparotomy, or more invasive techniques such as general open surgical procedures. Other techniques are listed in the table below. In some embodiments, particularly in the case of mammalian animals, the maternal animal is administered non-steroidal anti-inflammatory drugs (NSAIDs) before transplantation of the first xenogenic tissue into the fetal recipient animal, and preferably at least 1 hour before transplantation (followed by a second injection about 24 hours after surgery). Examples include flunixin meglumine, meloxicam, firocoxib, carprofen, and the like. In some embodiments, the maternal animal is administered antibiotics before transplantation of the first xenogenic tissue into the fetal recipient animal.

Transplantation of the first xenogenic tissue is carried out before immune system development in the pre-natal recipient animal, and more particularly before development of the cell-mediated immune system. Thus, the pre-natal recipient animal is a "pre-immune" animal, which means that the adaptive immune system of the animal is not yet developed. The period of gestation/incubation as well as the target pre-immune period for xenotransplantation varies from species to species. The table below outlines target developmental periods for various animals that could be used in the invention, it being appreciated that such information is generally well known or readily accessible for various additional animals.

TABLE

Gestational and post-natal dates for pre-immune fetal transplants.

| Species | Approximate Average Gestation length[4] | Approximate Pre-immune transplant time period[4] | Technique | Approximate post-natal transplant age (days/weeks after birth) |
|---|---|---|---|---|
| Pig | 115 days | <60 days Preferably, 35-59 days | Laparotomy, trans-uterine | 3-6 weeks, preferably at least 1 week after weaning†, more preferably at least 2 weeks after weaning |
| Goat | 150 days | ≤65 days Preferably, 35-60 days | Transcutaneous, ultrasound, or laparotomy, trans-uterine | 2 days to 6 weeks* |
| Sheep | 150 days | ≤65 days Preferably, 35-60 days | Transcutaneous, ultrasound, or laparotomy, trans-uterine | 2 days to 6 weeks* |
| Cow | 285 days | ≤75 days Preferably, 35-70 days | Laparotomy, trans-uterine or transcutaneous with ultrasound | 2 days to 6 weeks* |
| Mouse | 19-24 days | ≤20 days Preferably, 11-15 days | Laparotomy, trans-uterine | 3-6 weeks, preferably at least 1 week after weaning, more preferably at least 2 weeks after weaning |
| Rat | 21-24 days | ≤20 days Preferably, 13-17 days | Laparotomy, trans-uterine | 3-6 weeks |
| Hamster | 16 days | ≤14 Preferably, 11-14 days | Laparotomy, trans-uterine | 3-6 weeks |
| Guinea pig | 58-75 days | ≤35 days Preferably, 23-33 days | Laparotomy, trans-uterine | 3-6 weeks |
| Rabbit | 31 days | ≤20 days Preferably, 13-17 days | Laparotomy, trans-uterine | 4-6 weeks |

TABLE-continued

Gestational and post-natal dates for pre-immune fetal transplants.

| Species | Approximate Average Gestation length[A] | Approximate Pre-immune transplant time period[A] | Technique | Approximate post-natal transplant age (days/weeks after birth) |
|---|---|---|---|---|
| Chicken | 22 days | ≤15 days incubation Preferably, 4-12 days | Limb bud injection by candling to visualize embryo | 3-6 weeks after hatching |
| Albino Zebrafish | NA | 3.5-4.5 hours post fertilization | Micropipette transplantation to the blastodisc halfway between the margin and animal pole. | 10 days post-hatching |

[A]Day 0 is the onset of estrus indicated by the first day of male receptivity.
†"Weaning" refers to the last date on which the post-natal animal fed on the maternal animal's milk.
*Since milk replacers are available, weaning can be carried out at an early age after one or two feedings of colostrum.

After transplantation of the first xenogenic tissue, the pre-natal recipient animal is allowed to develop into a post-natal recipient animal. The term "post-natal" as used herein refers to the animal after completion of the fetal stage (or embryonic stage, depending on the species), which for the majority of animals, is the period after birth or hatching. The post-natal animal has a developed immune system, although it will be appreciated that the native immune system will continue to mature as the post-natal animal continues to develop outside of the womb or egg, after birth or hatching. In any event, it will be appreciated that the post-natal recipient animal is immunocompetent.

After birth or hatching, a second xenogenic tissue is transplanted into the post-natal recipient animal. In the case of mammalian recipient animals, the second xenogenic tissue is transplanted after weaning of the animal to avoid interference with the continued maturation of the animal's natural innate and adaptive immune systems. More preferably, the second xenogenic tissue is transplanted at least 1 week, and even more preferably at least 2 weeks after weaning of the animal. In some embodiments, this has been found to be a critical step, as it avoids interference by naturally-occurring, maternally-transferred antibodies. The age of weaning will depend on the species, but is some embodiments is about 3 weeks after birth.

The second xenogenic tissue is from the same "source" as the first xenogenic tissue. This means that the tissue and/or cells of the second xenograft are from the same cell culture, tissue resection, and/or biopsy as the tissue and/or cells used for the first xenograft. The second xenogenic tissue can be transplanted using various techniques depending upon the type of the tissue and/or cells used for the xenograft and the desired outcome and/or inquiry to be made. The second xenograft can be transplanted orthotopically or heterotopically. In one or more embodiments, the second xenogenic tissue can be transplanted subcutaneously via an injection. In one or more embodiments, the second xenogenic tissue can be transplanted directly into a target organ of the animal, using minimally invasive techniques, such as by percutaneous or transcutaneous injection, endoscopy, and/or laparotomy, or more invasive techniques such as general open surgical procedures. Preferably, however, the second xenogenic tissue is transplanted intravenously into the post-natal (and post-weaned, if applicable) animal. In one or more embodiments, the second xenogenic tissue is first supported in a gel matrix or scaffold prior to transplantation. Exemplary gel matrices include those derived from extracellular matrix (ECM), such as matrigel, or decellularized organs (lung, integument, mammary glands, etc.), as well as synthetic gels, such as agarose, alginate, polylactic acid, chitosan, and derivatives thereof.

After transplantation, the second xenogenic tissue is allowed to expand and in some cases engraft into the post-natal recipient animal, such that the animal eventually manifests a disease, malignancy, or condition associated with the transplanted xenogenic tissue (i.e., originating from and/or triggered by expansion of the xenogenic tissue in vivo in the recipient animal). For example, the xenogenic tissue can be used to generate tumors or chimeric tissues in the post-natal recipient animal. Advantageously, the post-natal recipient animal is immunologically tolerant to the xenogenic tissue, while remaining immunocompetent. Various types of cells and tissues can be used for the xenografts according to the invention. Non-limiting examples of xenogenic tissue that can be used in the invention include cancer cells, tumors, cancerous tissue, immune cells, stem cells, liver, epithelial, glial, erythroid, muscle cells, endothelial cells, and combinations thereof. Various types of stem cells include cancer stem cells, induced pluripotent stem cells, hematopoietic stem cells, mesenchymal stem cells, Wharton's jelly (umbilical) stem cells and engineered stem cells. The cells can be intact or homogenized. In one or more embodiments, the stem cells are immortalized, such as by ectopic expression of telomerase before xenotransplantation.

Cancer cells, tumors, or cancerous tissue can be used to establish cancers, including for example, pancreatic, breast, brain, bone, lung, melanoma, mesothelioma, prostatic, neuroblastoma, gastric, esophageal, skin, renal or colorectal solid (tumor based) cancers, as well as leukemia, lymphoma, or myeloma cancers. For example, tumors can be grown in the post-natal recipient animal to generate an immunocompetent animal model of cancer. An active agent, such as a chemotherapeutic or immunotherapeutic could then be administered to the post-natal recipient animal, followed by determining the effects of the active agent on the tumor. Such active agents could be delivered directly to the tumor or systemically administered (e.g., via injection, orally, intranasally, etc.) to the animal. Patient-derived cells can also be used to establish patient-specific tumors or other conditions in the recipient animal. In one or more embodiments, the xenogenic tissue is human tissue or cells. In one or more embodiments, the xenogenic tissue is non-human tissue or cells.

Various animals can be used for the recipient animal depending on the desired animal model and condition to be analyzed. Non-limiting examples include small and large animals, including rodents (mice, rats, squirrels, prairie dogs, porcupines, beavers, guinea pigs, and hamsters), rabbits, chickens, porcine (e.g., micro-, mini-, or domestic pigs), dogs, bovine (cattle), ovine (sheep), caprine (goats), or zebra fish. Such animal models have various uses for modeling and studying disease and treatments. In one or more embodiments, the animals are useful as models for human disease, and methods of modeling human disease using the inventive animal models are described herein.

For example, cancers could be established in the recipient animal via the second xenograft for advanced testing of pharmaceuticals, cytotherapy, photodynamic therapy, magnetic hyperthermic therapy, gene therapy, and the like. As noted above, a matrix can be used to transplant the cancer tissue, for example, where it would be desirable to restrict movement by the tumor cells to facilitate tumor formation. Similarly, pancreatic cancer cells could be transplanted into the post-natal recipient animal pancreas orthotopically via endoscopy or laparotomy, or could be transplanted percutaneously into the spleen for subsequent establishment of liver metastases. Hepatocellular carcinoma could be transplanted into the liver of the post-natal recipient animal without an abdominal incision by transcutaneous injection. For models of brain tumors, glioma cells could be transplanted into the cerebrum of the post-natal recipient animal. Similarly, breast cancer cells could be transplanted orthotopically into the mammary fat pad of the post-natal recipient animal. Other cancer cells could be given intravenously to establish metastatic tumors in the post-natal recipient animal. Bone cancer cells can be transplanted into the bone marrow cavity of post-natal recipient animals.

The immunocompetent, tolerogenic animal model would be an excellent way to study cancer stem cells, an area of intense interest in cancer research. The data demonstrates that the recipient animals did not reject the human tumor cells, and the transplanted cells appeared to be responding to environmental cues to differentiate into hepatocyte-like or bile duct lining cells in the liver, renal tubule-like cells in the kidney, and alveolar lining cells in the lung. Since tumors contain a subpopulation of cells with features of primitive stem cells it might be possible to re-isolate these engrafted cells to compare to the parental population.

This model may also allow the characterization of patient-derived conditions, such as patient-specific tumors. Various types of chemotherapies and/or immune therapies could then be tested in the animal model to determine which types of treatment might be the most efficacious for the patient.

In addition to cancer models, the inventive animal models could be applied to many other situations/diseases by uses various types of xenografts. For example, human induced pluripotent stem (iPS) cells could be tested in a more physiologically relevant model for their engraftment potential or whether they cause teratomas. For other cells such as derivatives of induced pluripotent cells, the animal model can be post-natally transplanted with cardiac or muscle cells. Other cells such as hematopoietic stem cells or mesenchymal stem cells could also be transplanted. Stem cells engineered to express therapeutic proteins could be transplanted, followed by induction of a disease entity to assess the cell's ability to abrogate a disease. For example, they could be engineered to express ILRa, a potent anti-inflammatory protein, and degenerative osteoarthritis could subsequently be induced in the animal model using established techniques. Proteins such as antibodies could be produced in large quantities from xenotransplanted human lymphocytes, plasma cells, myeloma cells or hybridomas.

The co-transplantation of stem or immune cells along with the tumor cells would tolerize the post-natal animal to those cells as well as the tumor cells. Thus, the stem cells or immune cells could be used to test various cell-based therapies.

Hematopoietic stem cells that are immortalized could also be xenotransplanted. For example, human, canine, equine, or feline red blood cells could be xenotransplanted, as described above, and then expanded and produced in the postnatal pig from erythroid or hematopoietic stem cells (after purification from the pig's red blood cells). These cells could be used for therapy for trauma or other clinical scenarios that require red blood cells currently often in short supply. Alternatively, patient-specific, immortalized hematopoietic stem cells could be transplanted in utero and then post-natally to allow production of patient-specific white blood cells for a chemotherapy patient. Since such therapeutic cells could be generated in large numbers in the xenotransplanted recipient animal, especially large animals, they would serve as a bioreactor to produce cell quantities that would normally be difficult or impossible to achieve with cell culture.

Other animal disease models could be established. For example, human muscle cells lacking dystrophin expression could be transplanted and tested for responses to new therapeutic approaches. Human liver cells engineered for reporter gene expression if certain toxic metabolites are formed could be analyzed. Likewise, human cells in chimeric pigs could be used to establish human viral infections to test new anti-viral therapies.

In addition to xenotransplantation of human cells, it would be advantageous to use other species. For example, mouse tumors could be established in a large animal model, so that after a therapy is shown to be successful against the mouse tumor in mice, the same therapy could be validated in a large animal model. This will allow treatments that work in the mouse to be tested on the same tumor type in a species that is much more relevant to humans with regard to physiology and size.

The animal models can also be used to expand xenogenic tissue in the animal model, followed by harvesting the expanded xenogenic tissue. The harvested tissue can be used for additional research, drug screening, etc., but could also be transplanted (or in the case of patient-derived xenogenic tissue, re-transplanted) into a patient or subject corresponding to the same species as the xenogenic tissue. Alternatively, the harvested xenogenic tissue can be serially transplanted into a second pre-natal recipient animal, according to the methods described above, followed by allowing that animal to develop into a post-natal recipient animal.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

General Procedure for Porcine Model

Tumor injection in fetuses. A pregnant sow at approximately 50 days gestation is anesthetized and given a dose of banamine. After induction of general anesthesia, a paramedian incision is made in the lower abdomen in order to externalize the uterus. The uterus is externalized, one horn at a time, and fetuses are palpated, isolated and immobilized. The fetuses are injected with human tumor cells (1-4 million cells) into the peritoneal cavity and/or the fetal liver using either ultrasound guided injection or landmark guided injection. Alternatively, cells are transplanted into the amnion or amniotic sac of the fetus. After all fetuses are injected, the uterus is replaced and the incision was sutured. The sow is watched closely for 24 hours. At 24 hours, another dose of banamine is given, as well as a broad spectrum antibiotic.

Remainder of gestation and post-farrowing: The sow is monitored closely during the remainder of gestation. At farrowing, 1-2 piglets are euthanized and the presence of tumors are analyzed for persistence and growth. After farrowing, the remaining piglets are allowed to nurse on the sow until weaning (approximately 3 weeks).

Post-natal tumor injection in piglets. One to several days after weaning, piglets are anesthetized and given a subcutaneous (or orthotopic or intravenous) injection of human tumor cells (the same tumor cell culture used above, 1-4 million cells). Two piglets are not given injections in order to monitor the ability of the fetal-injected to cells to develop tumors post-natally. The pigs are monitored for 120 days for the development of tumors. Any observable tumors are measured daily for progression during the 120 days. At 40-120 days the piglets are euthanized and any observable tumors are collected along with samples of liver and lung. In the experimental setting, any endpoint can be applicable. For example, after a course of drug or cell-based therapy, pigs can be monitored for health status and euthanized when clinical signs become evident (essentially a survival study). Another potential endpoint may occur if imaging (for example, using a large animal CT system) reveals internal tumors.

Post-study analysis: Tissues collected from the piglets were fixed in paraformaldehyde for IHC. Fixed tissues were analyzed by IHC using a variety of human specific markers to identify human-derived tumors in the piglets.

Example 2

Porcine Model

An experiment was carried out following the protocol described above in Example 1. Before farrowing, the sow developed sepsis and lost most of the fetuses. At farrowing, one live piglet was recovered. To determine the effectiveness of the procedure, this piglet was euthanized and tissues were collected. Liver was fixed and sectioned and probed with anti-human nuclear antibodies. IHC demonstrated the presence of small pockets of human cells in the liver. This indicates the fetal injections were successful and desensitized the developing fetus to human cells. In FIG. 1, brown staining indicates detection of human cells by anti-human antibodies at the surface of the liver.

Example 3

Porcine Model

A second experiment was carried out according to the protocol for Example 1, except that human triple negative breast cancer cells (MDA-MB-231) were transplanted into the pre-immune fetuses. In this case, nine live piglets were born. Two days after weaning, cells from the same cell culture were transplanted in a subcutaneous location in an ear of each piglet.

Figure 2:
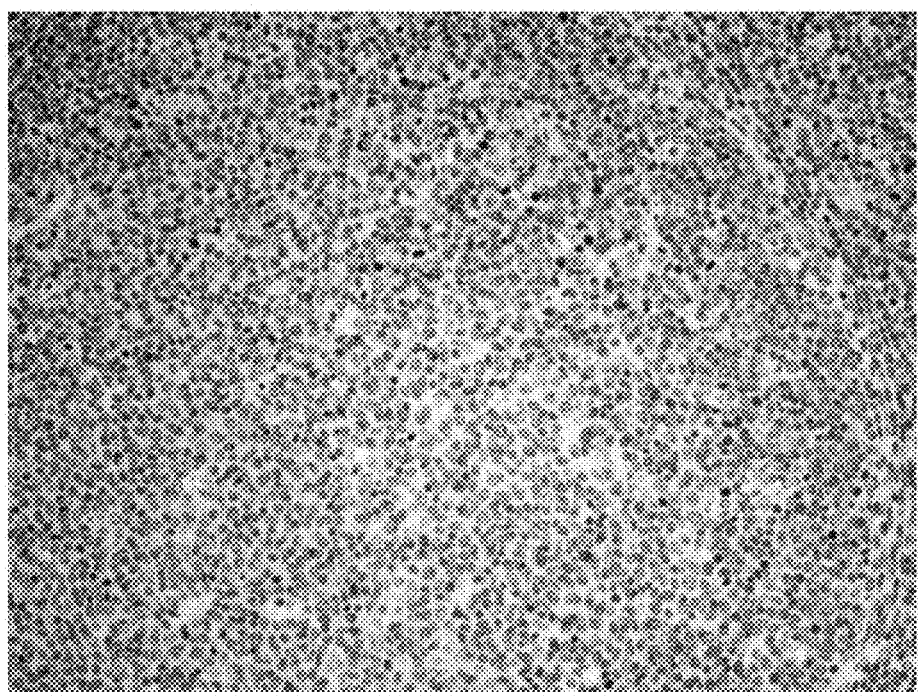
FIG. 2 is an anti-human nuclei IHC image of human cells incorporated in the immunocompetent (IC) pig retropharyngeal nodes.
Figure 3:
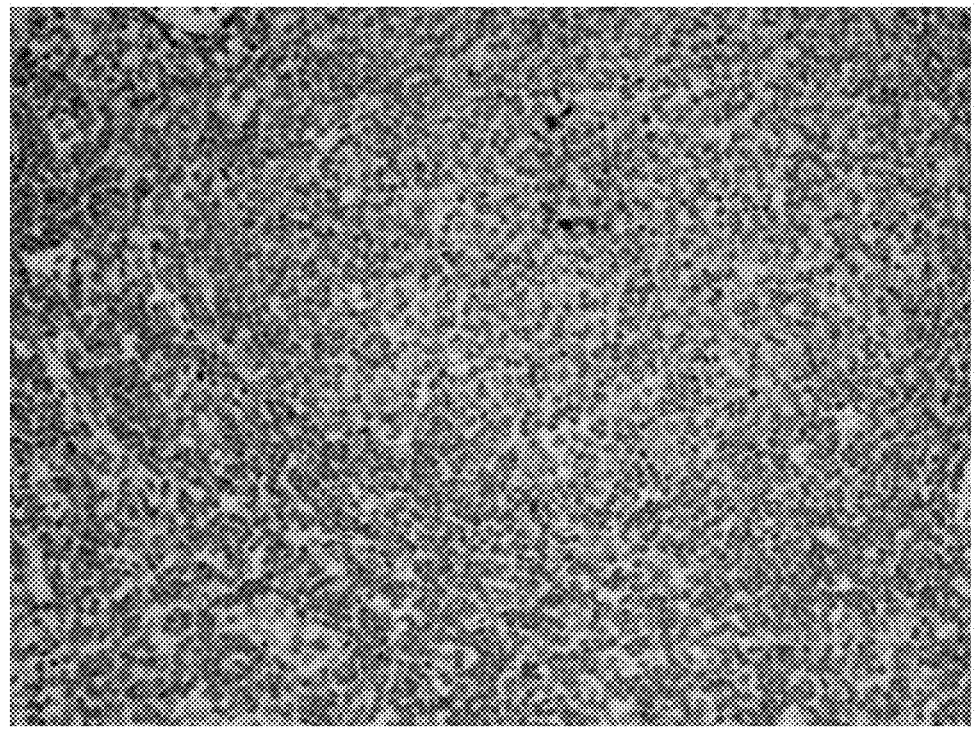
FIG. 3 is an anti-human nuclei IHC image of human cells incorporated in the IC pig mesenteric lymph nodes.
Figure 4:
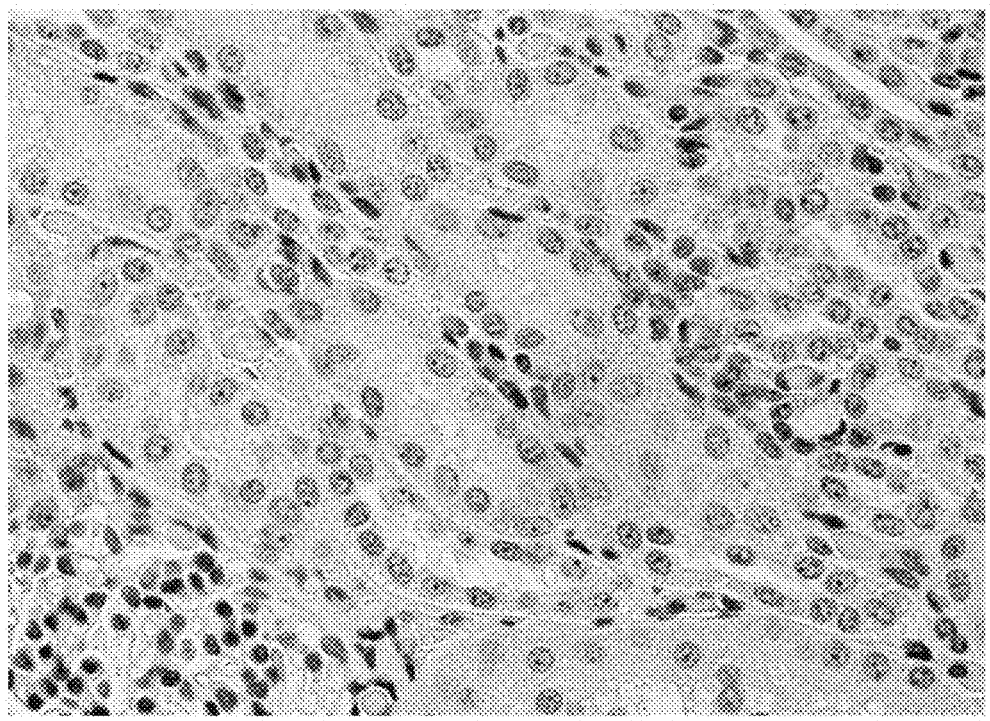
FIG. 4 is an anti-human nuclei IHC image of human cells incorporated in the IC pig thymus, adrenal cortex, lung, and kidney.
Figure 5:
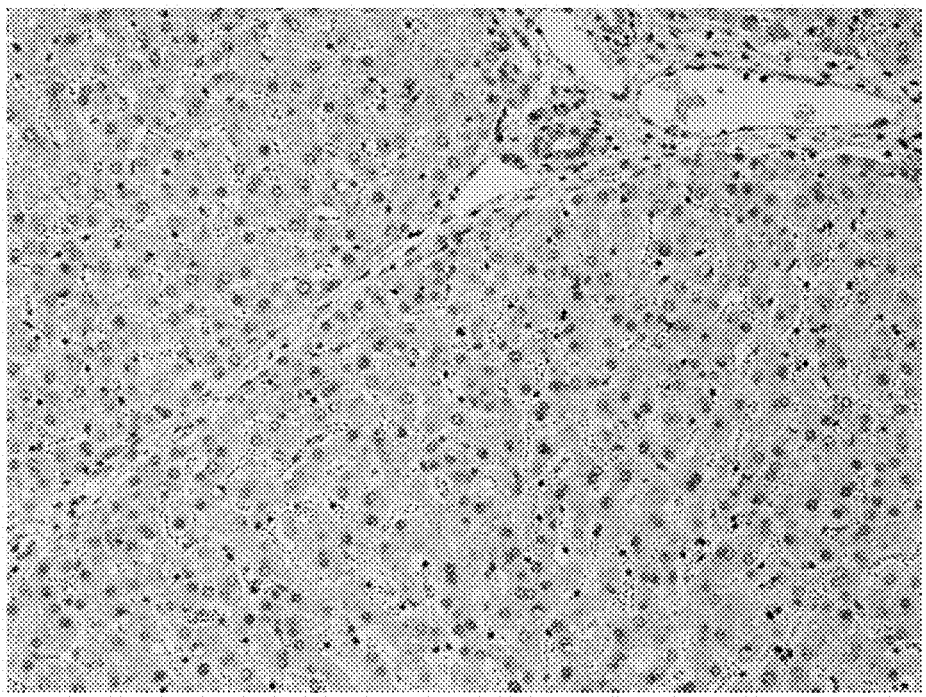
FIG. 5 is an anti-human nuclei IHC image of human cells incorporated in the IC pig liver.
Figure 6:
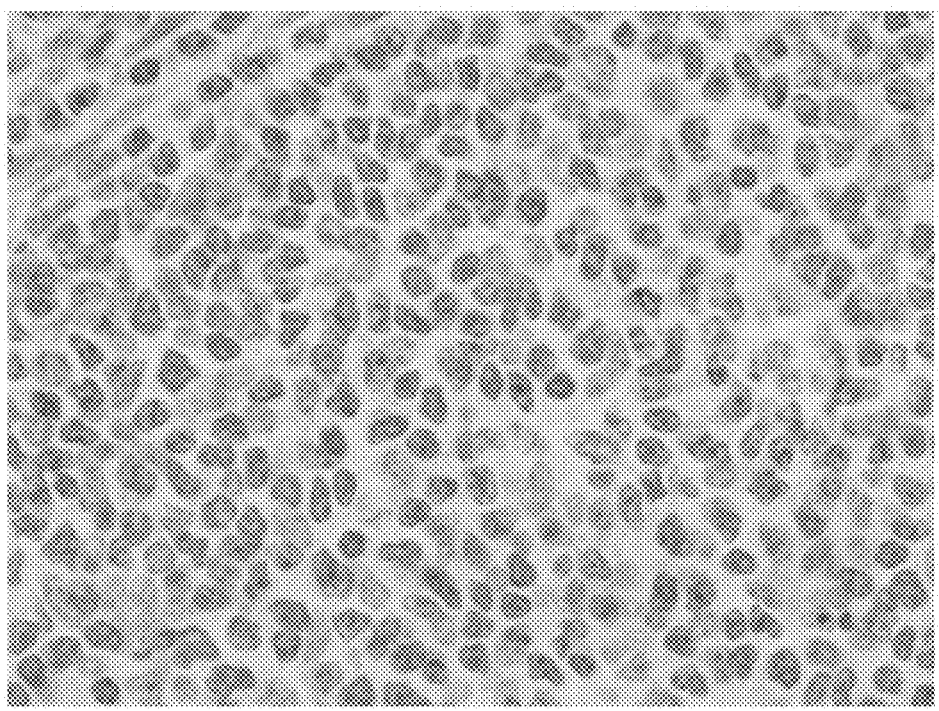
FIG. 6 is an IHC image of human cells incorporated into IC pig tissue after using a second human specific antibody against beta 2 microglobulin.

Analysis of tissues from this experiment showed many human cells incorporated in many pig tissues (identified by immunohistochemistry using a human specific anti-nuclear antibody) from the first in utero injection. Cells (brown in color) were found in retropharyngeal nodes (FIG. 2), mesenteric lymph nodes (FIG. 3), thymus, adrenal cortex, lung, kidney (FIG. 4) and liver (FIG. 5). Note that nearly 50% of liver cells have brown staining nuclei in FIG. 5 indicating that the breast cancer stem cell population responded to developmental cues of the developing liver. No positive cells were found in pigs not transplanted with human tumor cells. A second human specific antibody against beta 2 microglobulin identified additional positive cells (red color, FIG. 6).

Example 4

Validation in Small Animal Model—Rodent

Two pregnant CD-1 mice (one with 12 fetuses, one with 15) were anesthetized with isoflurane inhalation and subjected to a laparotomy incision. After exteriorization of uterine horns, mouse fetuses were transplanted with 50,000 human breast cancer cells intraperitoneally. Two live mouse pups were born. Although the attrition rate in this first experiment was high, the viable offspring illustrate that the in utero transplant in mice with human cancer cells is possible; future work will strive to increase the number of viable offspring.

Example 5

Porcine Model

Figure 7:
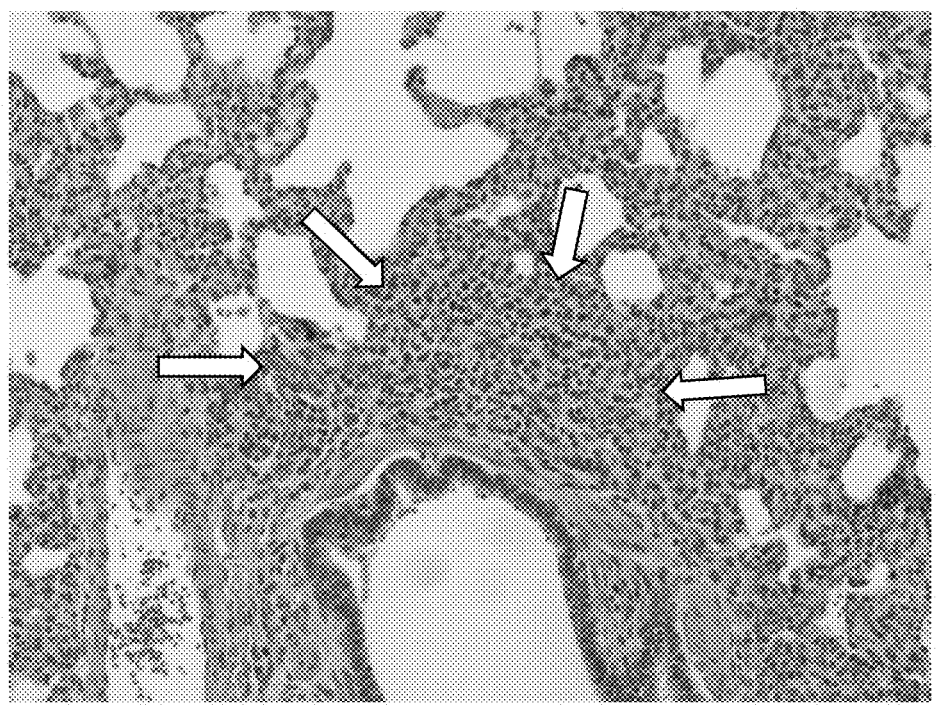
FIG. 7 is a hematoxylin and eosin (H&E) image of human cells incorporated into the pig lung and manifesting a cancerous lesion.
Figure 8:
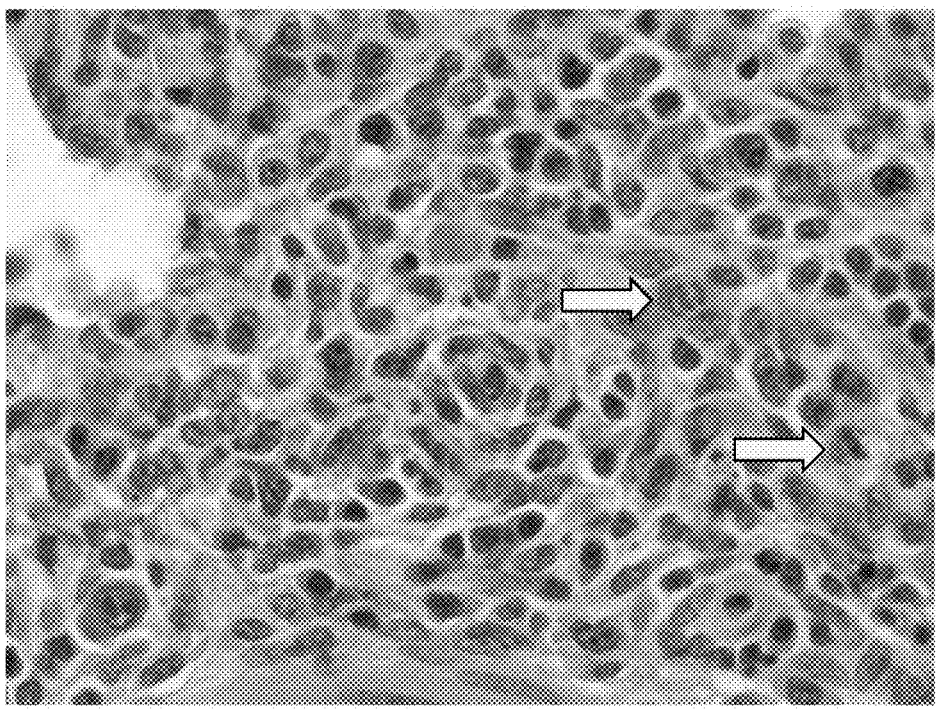
FIG. 8 is an H&E image of active cell division in the pig lung, associated with the presence of human cancer cells in the pig lung.
Figure 9:
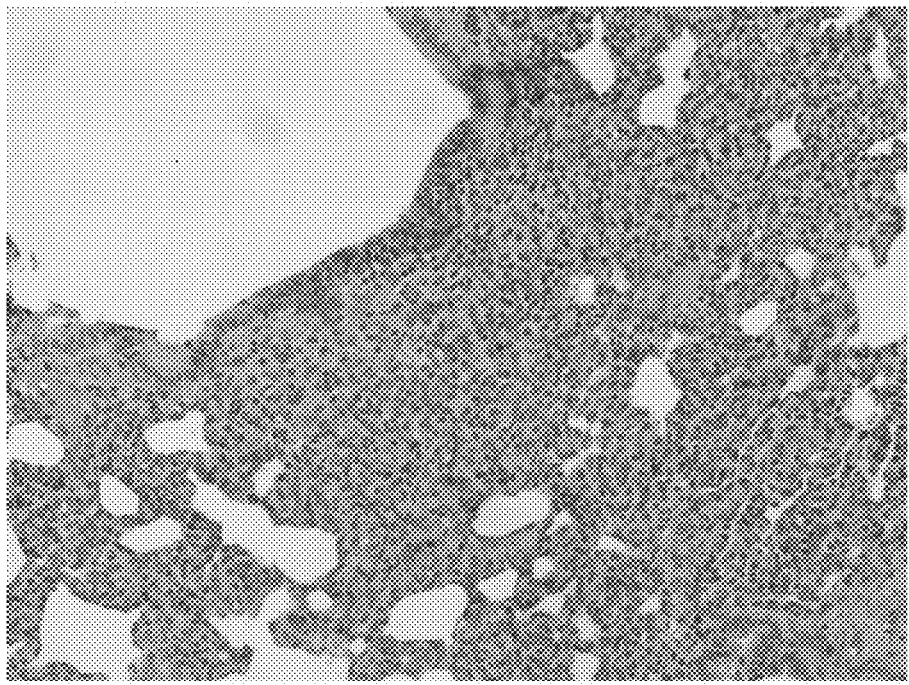
FIG. 9 is an H&E image of human cells in the pig lung.
Figure 10:
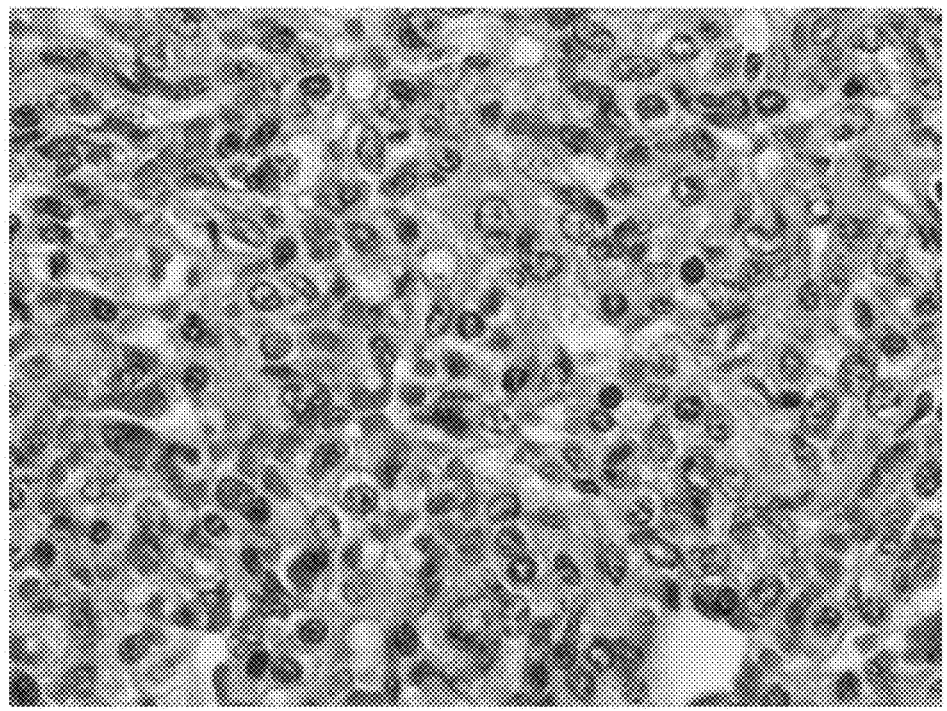
FIG. 10 is a magnified H&E image of human cells in the pig lung.
Figure 11:
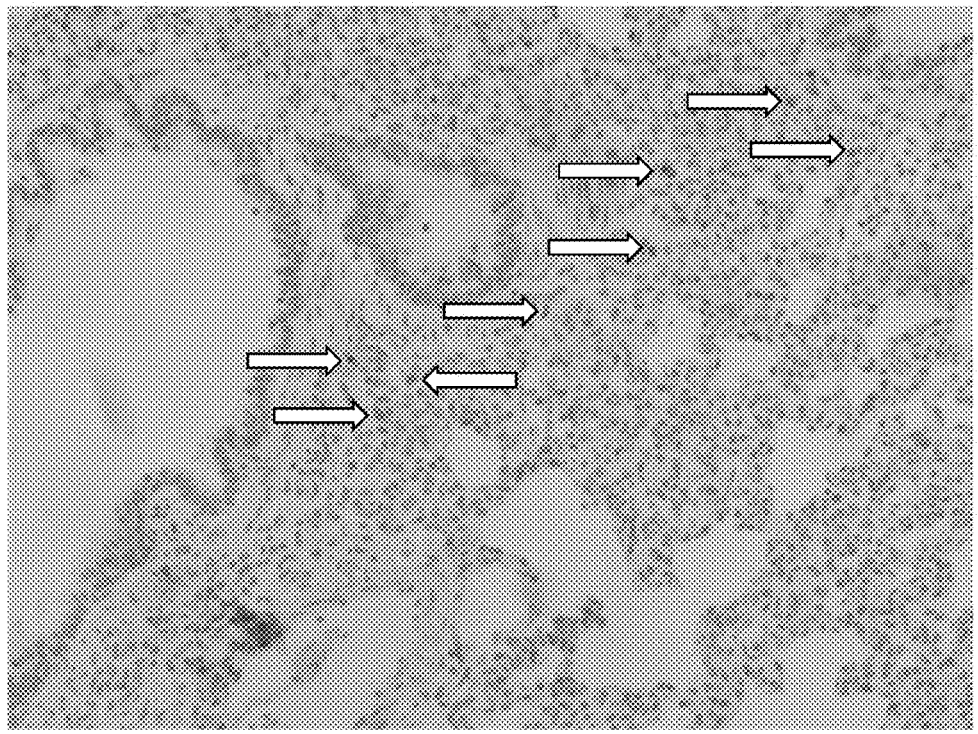
FIG. 11 is an IHC image of human cells in the pig lung as evidenced by the staining (red) of survivin in the human cancer cells.
Figure 12:
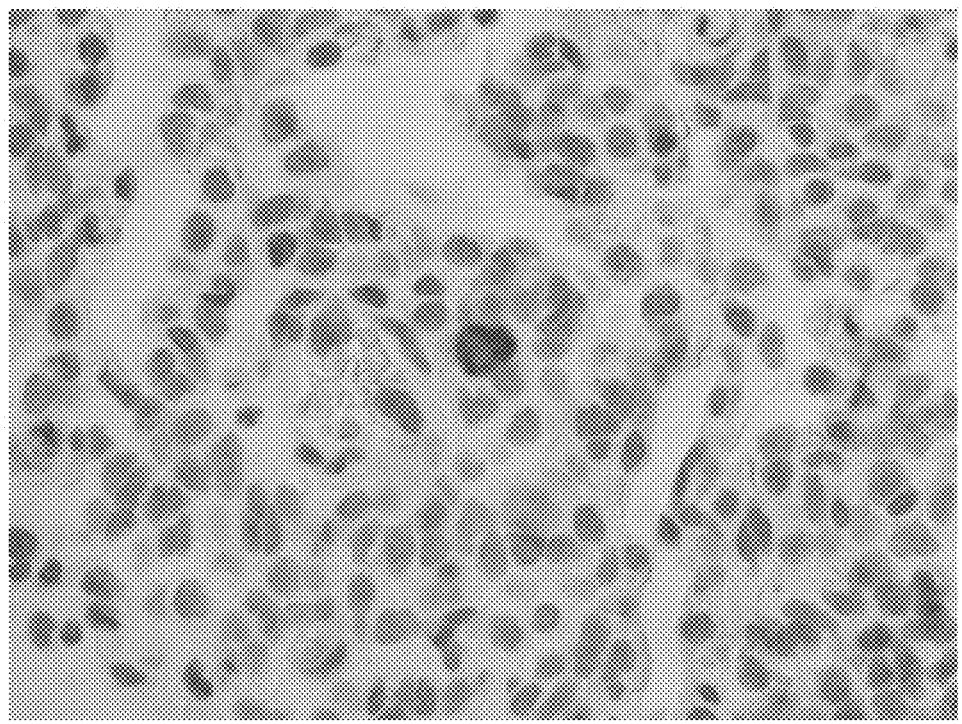
FIG. 12 is a magnified IHC image of a survivin-positive cell (red staining) in the pig lung.

An additional experiment was carried out according to Example 3, using the human breast cancer cells. The same protocol was followed as described above, with the important exception that the post-natal transplants of the breast cancer cells (10×10$^6$) were administered intravenously rather than subcutaneously. In addition, the post-natal transplant was carried out two weeks after weaning (i.e., about 5 weeks after birth). As can be seen from the figures, tumors were found throughout the lungs of the re-transplanted, immunocompetent, tolerized piglets 80 days after the re-transplantation. As indicated by the arrows in FIG. 7, a human breast cancer lesion was identified in the pig lung tissue. Active cell division was also observed as indicated by the arrows in FIG. 8, which is indicative of cancer cells (and unexpected for normal lung tissue). FIG. 9 shows another human breast cancer lesion in the piglet lung tissue, with high magnification of the lung tissue being shown in FIG. 10. Immunohistochemistry staining was carried out on the tissue using human-specific rabbit monoclonal antibody. As shown in FIG. 11, survivin-positive cells were observed in the human breast cancer lesion in the piglet lung tissue (red staining, arrows). Survivin is a cancer-specific protein found in a subset of cancer cells known as cancer stem cells. FIG. 12 provides a high magnification image of a survivin-positive cell (red staining) in the human breast cancer lesion in the piglet lung tissue.

Example 6

Small Animal Model—Rodent

Figure 13:
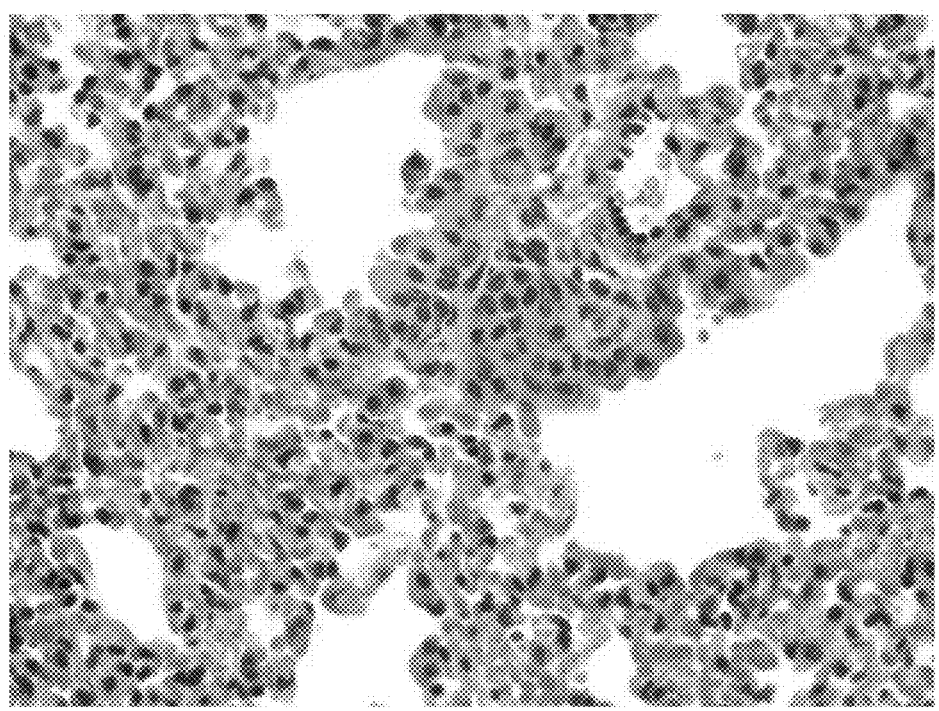
FIG. 13 is an H&E image of human breast cancer cells in the immunocompetent (IC) CD-1 mouse lung.
Figure 14:
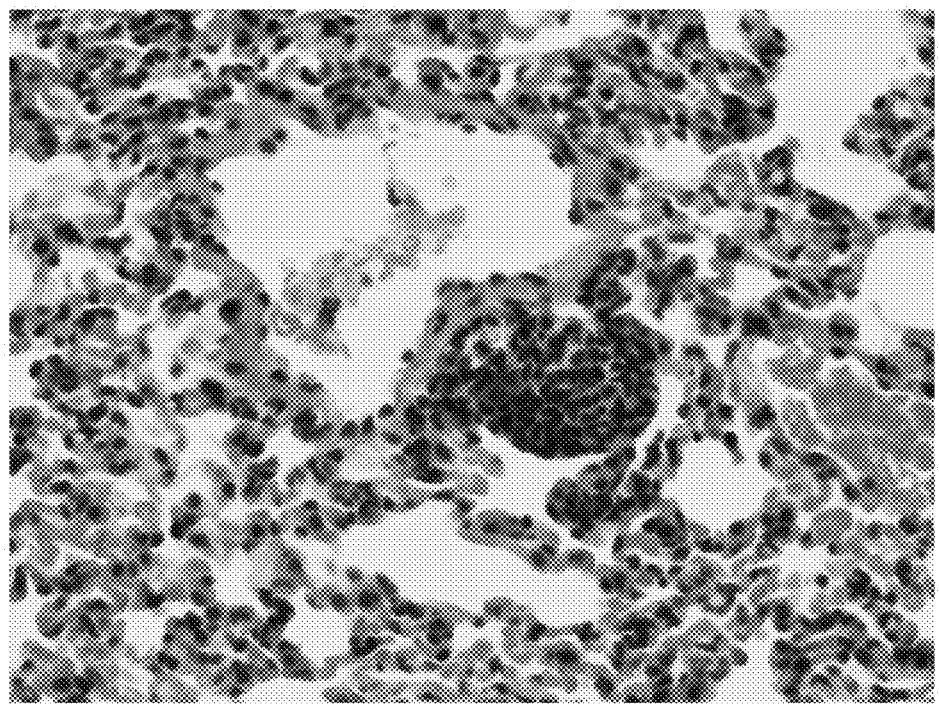
FIG. 14 is an H&E image of human M21 melanoma cells in the IC CD-1 mouse lung.
Figure 15:
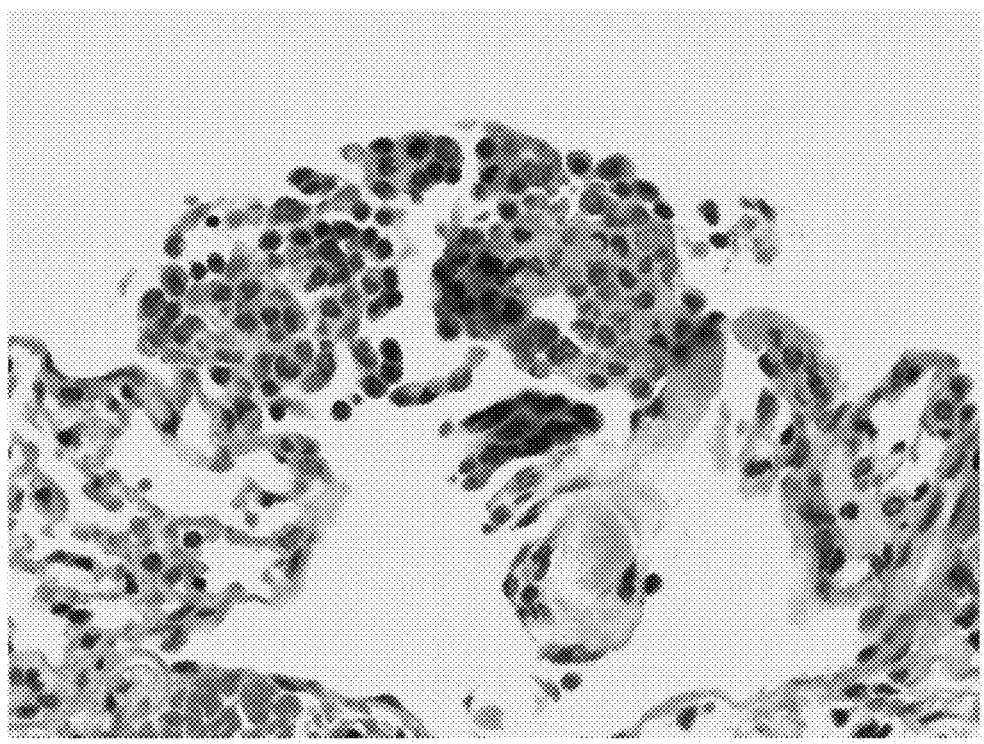
FIG. 15 is an H&E image of human pancreatic cancer cells in the IC CD-1 mouse lung.
Figure 16:
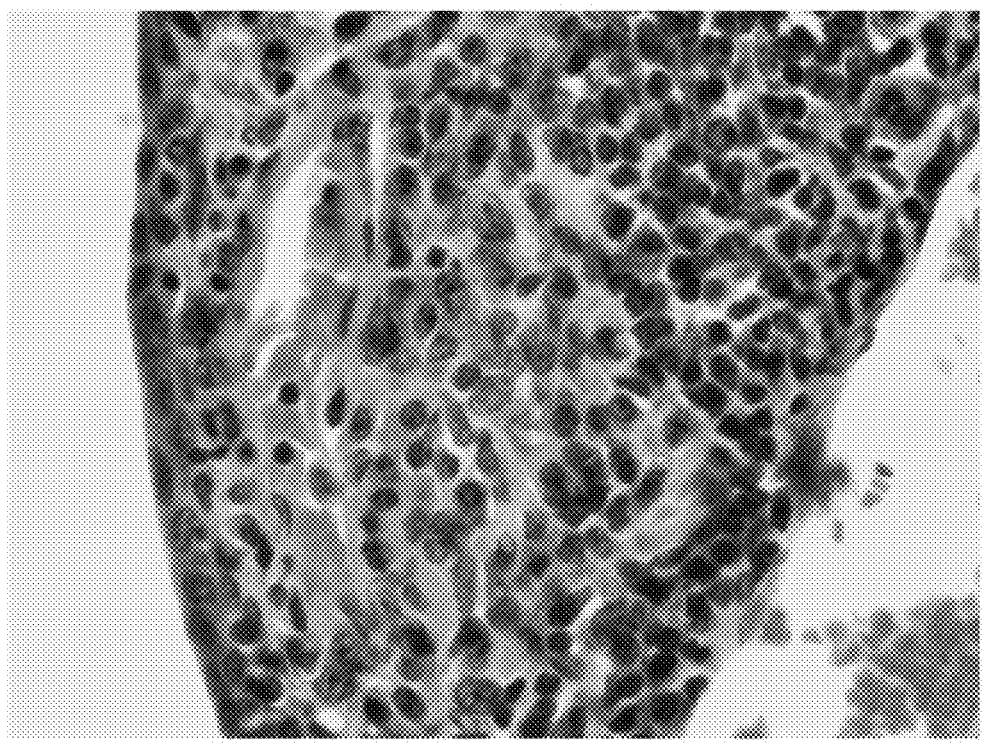
FIG. 16 is an H&E image of human pancreatic cancer cells in the IC CD-1 mouse kidney.
Figure 17:
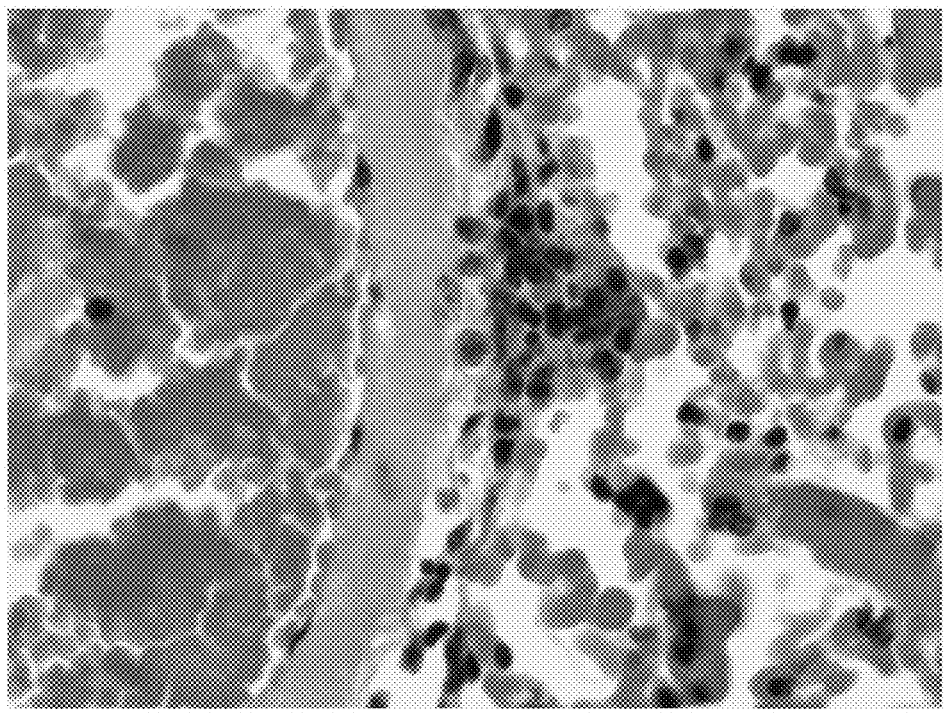
FIG. 17 is an H&E image of human cervical cancer cells in the IC CD-1 mouse lung.
Figure 18:
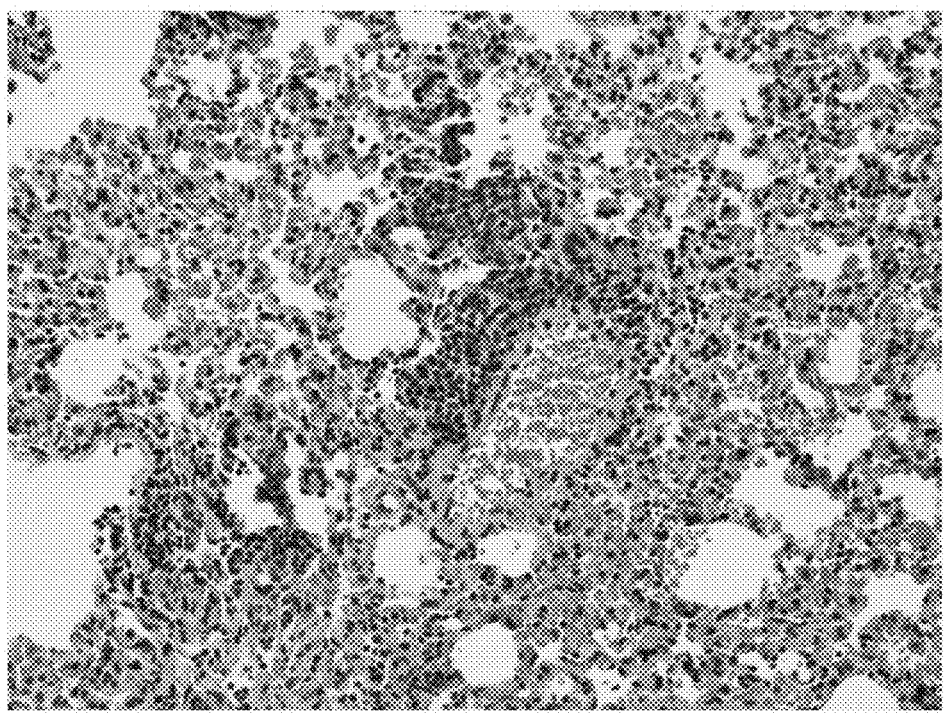
FIG. 18 is an H&E image of human A375 melanoma cancer cells in a Balb/c IC CD-1 mouse lung.

Additional mouse experiments were carried out as described in Example 4 above. A critical modification was to use intra-amniotic transplantation of the xenogenic tissue rather than intraperitoneal during the in utero injections to result in many more viable mouse pups for later re-transplant. This underscores the importance of this finding during the course of these experiments. All human cell lines resulted in tumors after intravenous re-transplant two weeks after weaning (about 5 weeks after birth). The following human cancer cells were transplanted in utero for tolerization in CD-1 or Balb/c mice followed by the second transplant after weaning: MDA-231, human breast cancer; M21 human melanoma; BxPC3, human pancreatic cancer; HeLa, human cervical cancer. In addition, the A375 human melanoma cells we showed previously to develop tumors were transplanted into mice of a different strain (Balb/c) to show the procedure could be used successfully across different mouse strains. The results are shown in the figures which are images of the lung tissue from the mice. FIG. 13 is an image of the mouse lung tissue showing the human breast cancer cells in the immunocompetent mouse lung. FIG. 14 is an image of the M21 human melanoma cells in the immunocompetent mouse lung. FIG. 15 is an image of the human pancreatic cancer cells in the immunocompetent mouse lung. FIG. 16 is an image of the human pancreatic cancer cells in the immunocompetent mouse kidney tissue. FIG. 17 is an image of the human cervical cancer cells in the immunocompetent mouse lung. FIG. 18 is an image of the human A375 melanoma cells in a Balb/c immunocompetent mouse lung.

What is claimed:

1. A method of producing an immunocompetent non-human mammalian model having immunological tolerance to a xenograft, said method comprising:
  transplanting first xenogenic cells into a pre-natal recipient mammal, wherein said recipient mammal is a pre-immune, fetal or embryonic non-human mammal;
  allowing said pre-natal recipient mammal to develop into a post-natal recipient mammal; and
  transplanting second xenogenic cells into said post-natal recipient mammal via intravenous injection of said second xenogenic cells, wherein said second xenogenic cells are from the same source as said first xenogenic cells, wherein said post-natal recipient mammal is immunocompetent, said post-natal recipient mammal being immunologically tolerant to said second xenogenic cells, wherein said second xenogenic cells are transplanted into said post-natal recipient mammal after weaning.

2. The method of claim 1, wherein said transplanting said first xenogenic cells comprises injecting said first xenogenic cells into the amnion surrounding said pre-natal recipient mammal.

3. The method of claim 2, said first xenogenic cells being injected while said pre-natal recipient mammal remains in utero of a maternal mammal carrying said pre-natal recipient mammal.

4. The method of claim 1, wherein said pre-natal recipient mammal develops into said post-natal recipient mammal via birth.

5. The method of claim 4, wherein said weaning occurs at least 3 weeks after said birth.

6. The method of claim 1, wherein said second xenogenic cells are transplanted into said post-natal recipient mammal at least one week after weaning.

7. The method of claim 1, wherein said xenogenic cells are cancerous, wherein said second xenogenic cells develop into a tumor in said post-natal recipient mammal.

8. The method of claim 7, further comprising administering an active agent to said post-natal recipient mammal and determining the effect of said active agent on said tumor.

9. The method of claim 7, further comprising subjecting said mammal to a therapy selected from the group consisting of cytotherapy, photodynamic therapy, magnetic hyperthermic therapy, and gene therapy, and determining the effect of said therapy on said tumor.

10. The method of claim 1, wherein said xenogenic cells are selected from the group consisting of cancer cells, immune cells, stem cells, liver cells, epithelial cells, glial cells, erythroid cells, muscle cells, endothelial cells, and combinations thereof.

11. The method of claim 10, wherein said stem cells are selected from the group consisting of cancer stem cells, induced pluripotent stem cells, hematopoietic stem cells, mesenchymal stem cells, engineered stem cells, and combinations thereof.

12. The method of claim 1, wherein said xenogenic cells are human cells.

13. The method of claim 1, further comprising allowing said second xenogenic cells to expand in said post-natal recipient mammal and harvesting said expanded xenogenic cells from said post-natal recipient mammal.

* * * * *